United States Patent
Sambusseti

(10) Patent No.: US 10,368,992 B2
(45) Date of Patent: Aug. 6, 2019

(54) RESORBABLE AND BIOCOMPATIBLE GRAFT IN PGA FOR IMPLANT FOLLOWING EXCISION OF THE IPP PLAQUE

(71) Applicant: Antonio Sambusseti, Cremona (IT)

(72) Inventor: Antonio Sambusseti, Cremona (IT)

( * ) Notice: Subject to any disclaimer, the term of this patent is extended or adjusted under 35 U.S.C. 154(b) by 45 days.

(21) Appl. No.: 15/547,456

(22) PCT Filed: Jan. 28, 2016

(86) PCT No.: PCT/EP2016/051843
§ 371 (c)(1),
(2) Date: Jul. 28, 2017

(87) PCT Pub. No.: WO2016/120409
PCT Pub. Date: Aug. 4, 2016

(65) Prior Publication Data
US 2018/0008414 A1   Jan. 11, 2018

(30) Foreign Application Priority Data

Jan. 30, 2015 (IT) .............................. MI2015A0127

(51) Int. Cl.
| A61F 2/26 | (2006.01) |
| A61F 2/00 | (2006.01) |
| A61L 27/18 | (2006.01) |
| C08L 67/04 | (2006.01) |
| A61F 5/41 | (2006.01) |

(52) U.S. Cl.
CPC .............. *A61F 2/26* (2013.01); *A61F 2/0063* (2013.01); *A61L 27/18* (2013.01); *C08L 67/04* (2013.01); *A61F 2005/411* (2013.01); *A61F 2210/0004* (2013.01); *A61L 2430/34* (2013.01)

(58) Field of Classification Search
CPC . A61F 2/0063; A61F 2210/0004; A61L 31/06
USPC ..................................... 600/38–41
See application file for complete search history.

(56) References Cited

U.S. PATENT DOCUMENTS

| 3,054,406 | A | * | 9/1962 | Usher | ................... A61F 2/0063 139/426 R |
| 4,520,821 | A | * | 6/1985 | Schmidt | ................ A61F 2/0063 435/399 |
| 5,292,328 | A | * | 3/1994 | Hain | ..................... A61F 2/0063 264/103 |
| 2008/0045784 | A1 | * | 2/2008 | Krakovsky | ............. A61F 2/105 600/38 |

FOREIGN PATENT DOCUMENTS

| IT | MI2011A000166 | 4/2011 |
| WO | 2011003422 | 1/2011 |
| WO | 2011064110 | 6/2011 |
| WO | 2012104380 | 8/2012 |
| WO | 2013135543 | 9/2013 |

* cited by examiner

*Primary Examiner* — Samuel G Gilbert
(74) *Attorney, Agent, or Firm* — Young & Thompson

(57) ABSTRACT

Disclosed is a graft for implant after excision of the IPP (induratio penis plastica) plaque due to Peyronie's disease. The graft is formed by a loom woven fabric, with low porosity, deriving from a monofilament or multifilament yarn of fibers of resorbable polymer in PGA (polyglycolide).

15 Claims, 3 Drawing Sheets

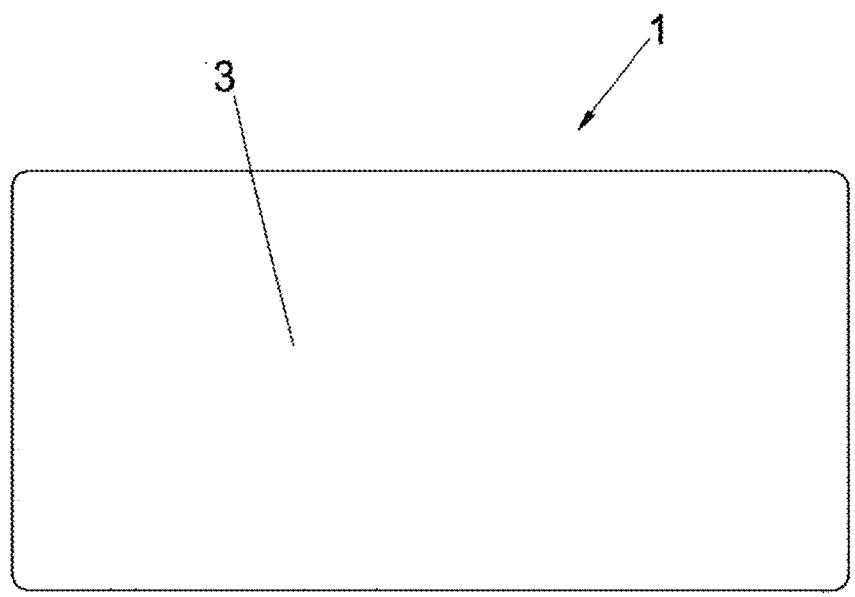
FIG. 1a
FIG. 1b
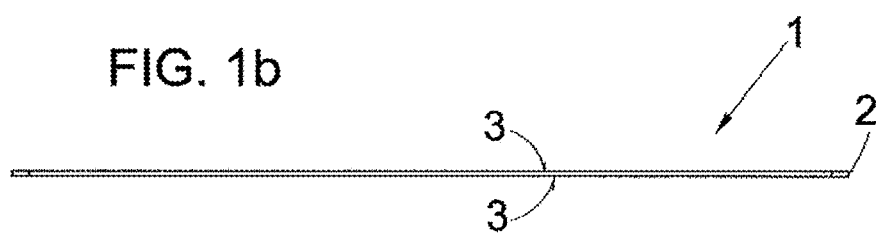

FIG. 3
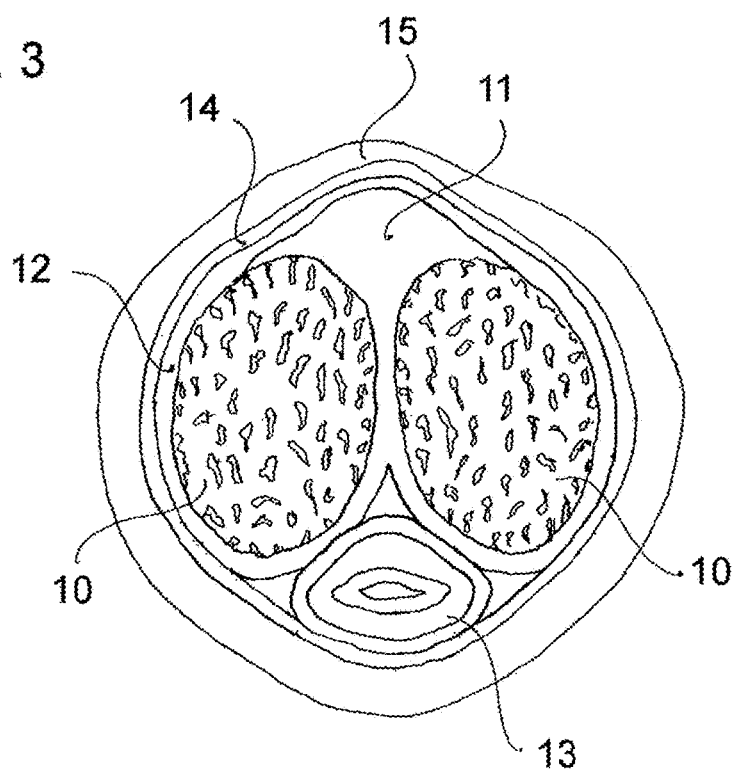
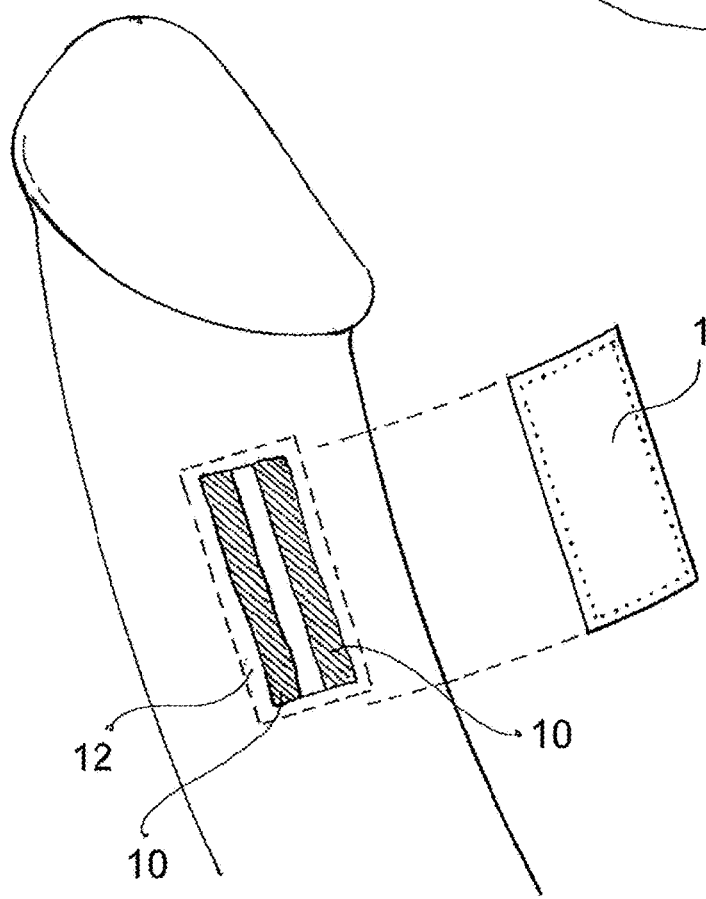
FIG. 2c

RESORBABLE AND BIOCOMPATIBLE GRAFT IN PGA FOR IMPLANT FOLLOWING EXCISION OF THE IPP PLAQUE

The present invention relates to an improved resorbable graft in PGA to be used in the field of urology, in particular as dermal implant in the excision of the IPP (induratio penis plastica) plaque as a result of Peyronie's disease.

More particularly the present invention relates to a resorbable graft, made of a low porosity woven fabric deriving from a yarn in PGA, suitable for being implanted as is without any coating of tissue cells deposited thereon, in particular of cells of the corpora cavernosa and/or of the tunica albuginea.

Peyronie's disease, whose cause is not yet well known, concerns the male genital organ and causes in it a varyingly accentuated penis deformity due to the presence of one or more hard fibrous plaques, with a nodular appearance, located above the corpora cavernosa of the penis, in particular at the level of the tunica albuginea (the sheath which covers the corpora cavernosa of the penis and which represents the load-bearing structure which causes the rigidity of the penis when erect) with irreversible degeneration of the albuginea elastic component.

The area of fibrosis, defined generically as "plaque", causes a curving of the penis towards the diseased side. This disease is associated with intense pain and erectile dysfunction in that the disappearance of the elastic fibres, which takes place in favour of the growth of the dense fibrous tissue of the plaque, constitutes an alteration of the mechanical characteristics of the corpora cavernosa.

When the disease has stabilised (since at least six months) and is such as to compromise sexual function, it is necessary to resort to surgical treatment such as surgery of the albuginea or complete excision of the plaque.

The current tendency is that of a complete excision (removal or cutting-out) of the plaque: in this case there is the consequent replacement of the section removed with a dermal implant or graft made up of autologous tissue (that of the patent, such as for example dermis of the thigh of the patient) in that a tissue is needed which undergoes a natural histo-transformation, maintaining the elastic fibres contained therein, in order to allow the restoring of the function of the organ: in filet in the processes of tissue repair the production of elastic tissue is not foreseen but only of fibrous tissue since in the cell matrix there are only fibroblasts and not elastoblasts.

The implants, also known as grafts, allow restoring of the original length on the side affected by the scar retraction shortening the penis, at the same time acting as support for the autologous tissue of the patient which will go to form with the passing of time over said graft.

The synthetic grafts in the corporoplasty technique mentioned above are not widely used to date in that their physiopathological features of engraftment do not allow reconstruction of a symmetrical and congruous cavernous albuginea envelope.

It is in fact known that their engraftment mechanism does not foresee vascular inosculation but only their fibroblast encapsulation. This would involve a structure for replacement of the albuginea without elastic fibres and therefore not extendable, and a fibrous reaction of the erectile tissue below the implant with tendency towards retraction.

In cases of serious erectile deficiency another type of surgical technique is used which involves the use of penis prostheses of various types (soft, malleable and hydraulic) in order to straighten and/or lengthen the organ and regain erection, in combination with autologous dermal grafts. However this technique entails a high percentage of infection complications when dermal grafts of the autologous type are used, due to the presence of *staphylococci*.

The use of heterologous grafts (SIS) or synthetic grafts (GORETEX), although avoiding the aforementioned complications, also does not guarantee the obtaining of a high elasticity due to their tendency towards retraction and the quality of the tissue reconstruction around them.

Another surgical technique consists of surgery for resection/incision of the plaque, excision of the albuginea and corpora cavernosa and implanting of a graft, preferably autologous, of the saphenous vein, between the albuginea and the corpora cavernosa. In this case too, according to the type of graft, the disadvantages stated above may occur.

Therefore it is highly desirable to have available implants, in particular synthetic grafts, which maximise the features of elasticity, almost as much as the original tissue, and lead to an improved quality of the tissue reconstruction with their creation of elastoblasts as well as fibroblasts without granulomas, keloids and the like, minimising the reaction of retraction to the implant, and infection reactions.

Resorbable synthetic grafts have also been described in the art, made with a mesh fabric of PGA or PLA, suitable for the replacement of the IPP (induratio penis plastica) plaque due to Peyronie's disease, following excision of the plaque itself. See for example the patent application MI2011A000166 in the name of the Applicant.

Nevertheless tests performed by the Applicant have shown that such a resorbable mesh fabric has numerous technical disadvantages.

The graft in PLA described therein has proved to be particularly unsuitable for implanting in that it has created inflammatory reactions both in intra use and under the skin, these tissues being absolutely comparable to the tunica albuginea.

Tests performed using the graft in PGA described therein have shown that this graft in PGA, with thickness of 600 microns and mesh structure, has a low impermeability to blood such as to be unsuitable for containing time leaks and the transpiration of the blood coming from the corpora cavernosa (which is of the artery type) due to the impossibility of being watertight.

Moreover this graft has been found to be unsuitable for the replacement of the tissues of the tunica albuginea, even if suitable for replacing other urological tissues, for example those of the bladder or ureter/urethra, due probably to an excessive weight of the tissue.

WO2011/064110 describes a planar patch in PGA fabric, reinforced with surface stiffening strips, to be used in the replacement of portions of bladder.

WO2013/135543 describes a dome in PGA fabric, mounted on a domed frame in bioabsorbable plastic, to be used to increase the volume of atrophied bladders.

The object of the present invention is to provide a graft for excision of the IPP which overcomes the disadvantages suffered in the prior art, in particular to provide a biocompatible and highly elastic graft which has a reduced formation of the fibrotic capsule around it, also when replacing an extended IPP plaque, and which can be used in any type of surgical operation without giving rise to infections.

Another object is that of providing such a resorbable graft which is lightweight and extremely waterproof, in particular with respect to blood of the artery type.

Yet another object of the present invention is that of providing such a graft which is also easy to produce and economical, as well as reliable, practical and absorbable in order to avoid a subsequent operation for removal of the graft.

These objects are achieved by the resorbable graft according to the invention in biocompatible material constituted by PGA which has the features of the annexed independent claim 1.

Advantageous embodiments of the invention are disclosed by the dependent claims.

The graft according to the invention for implant after excision of the IPP (induratio penis plastica) plaque due to Peyronie's disease is made with a non-texturised fabric, with low porosity and without reinforcements and/or support structure, which derives from the weaving or spinning of a monofilament or multifilament yarn of fibres of PGA (a biocompatible and resorbable polymer).

Said fabric is grafted in the patient with the outer surface free from any covering of cells and of any previous surface treatment for encouraging the engraftment of growing tissues.

Further features of the invention will be made clearer by the following detailed description referred to some of its embodiments purely by way of a non-limiting example, illustrated in the accompanying drawings, in which:

FIG. 1a is a plan view from above of an embodiment of the graft in accordance with the invention;

FIG. 1b is a side view of the graft illustrated in FIG. 1a;

FIGS. 2a-2c are views illustrating the possible positionings of the graft of FIG. 1a on the male genital organ respectively in ventral, dorsal and lateral position;

FIG. 3 is a cross-sectioned view of a male genital organ which has the IPP plaque.

Figure 2A:
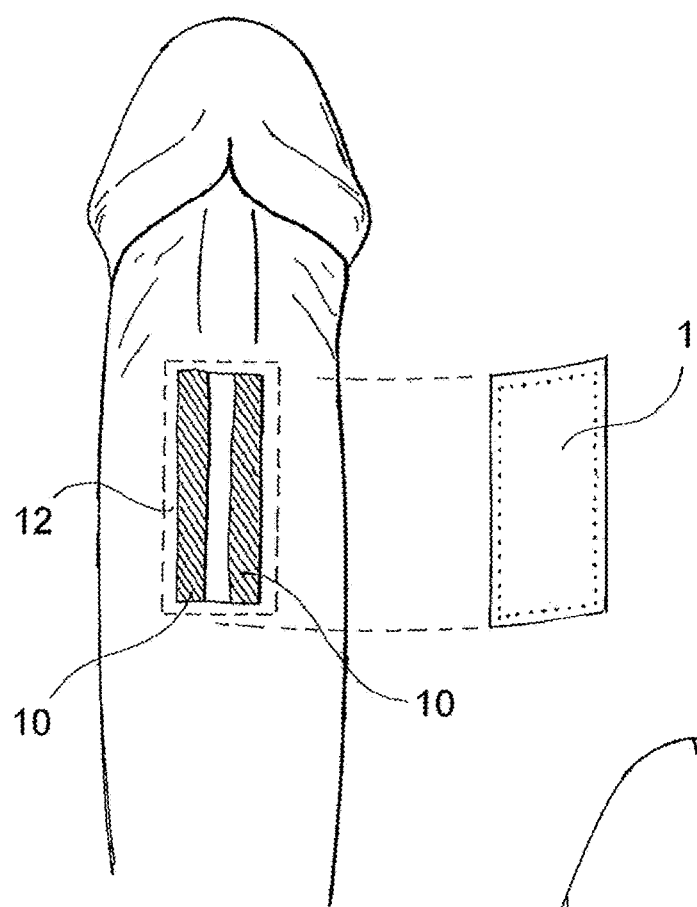

The graft 1 (FIGS. 1a and b) is in general flat, rectangular or square in shape, with dimensions which vary according to the possible approximate dimensions of the plaque.

A dimensional example of this graft is 5 cm×10 cm.

Said graft 1 is in the form of fabric 2 and its thickness is identical to that of the tunica albuginea and/or corpora cavernosa which it has to regenerate, generally lower than 600 microns, preferably lower or equal to 500 microns, more preferably comprised between 500 microns and 50 microns.

Said graft 1 in PGA is in the form of woven fabric which can be made using an ultra-lightweight monofilament or multifilament yarn, deriving from fibres of PGA (polyglycolide or polyglycolic acid), preferably homopolymer.

When a monofilament in PGA is used, the fabric 2 has a denier count (also defined as linear mass density) or basis weight lower than 240 deniers and the monofilament of PGA has a denier count lower than 120 deniers, where the deniers here refer to the diameter of the monofilament.

The term "deniers", D, indicates the weight of the textile, where 1 D corresponds to 9,000 meters of yarn with weight 9,000 g (P(g)/L (9,000 m)).

When the graft in PGA is constituted by a yarn of PGA fibres, it is preferably a multifilament yarn of 75 deniers/30 filaments (parallel one to the other).

The fabric 2 of the graft 1 in PGA can be made in various ways using said monofilament or multifilament yarn of PGA, preferably the abovementioned multifilament yarn of 75 deniers/30 filaments, using a loom for weaving, preferably of the shuttle loom type.

The loom weaving excludes the possibility of obtaining a knitted fabric, a nonwoven fabric or even a felt-like material.

This loom manufacture allows also a fabric to be obtained having a very low porosity, generally equal to or lower than 50%, thus allowing a high impermeability to viscous liquids to be achieved.

In a preferred embodiment the warp density—ends per cm, EPC and the weft density—counts per cm, CPC—is regulated so as to obtain a fabric having a porosity comprised within the range from 5% to 50%.

In order to obtain such a porosity range, the EPC varies within the range comprised between 50-100 ends/cm while the CPC varies in the range comprised within the range of 30-70 counts/cm.

The model of weaving (or weaving pattern) is a plain weave or planar weaving 1/1 which provides the greatest density and the lowest porosity of the fabric.

Greater densities can be achieved by subjecting the fabric obtained above to calendering. Calendering is a process of sizing which consists in applying to the fabric a pressure and heat, by means of calenders, in order to reduce the thickness of the fabric and reduce the porosity by closing the pores.

Typically the pressure applied by the calenders is within the range comprised between 200-400 bars and the temperature of sizing is in the range comprised between 45-85° C.

Therefore, by working appropriately on the regulation of the warp parameters (warp density—EPC) and weft parameters (weft density—CPC), on the pressure and temperature, it is possible to vary advantageously the porosity and the thickness of the fabric in the following ranges:

Thickness: 60-500 μm

Porosity: 0-50%.

The aforesaid yarns, as well as the thickness of the fabric resulting therefrom and the type of loom processing of the fabric, make the present resorbable graft 1 extremely lightweight and also extremely impermeable with respect to the blood of the artery type.

Moreover the present woven fabric or woven textile has such a mechanical consistency as to be able to be used alone without the need for support.

The manufacture of the graft 1 in textile form takes place in an environment with controlled contamination, in a white room and at reduced humidity (in the case of PLA). Once processing has finished the graft 1 is placed in a double blister closed with a sheet of Tyvek to avoid contaminations, and sent to a cycle of sterilisation with gamma rays. At this point the graft 1 is ready for use in an operation.

Figure 2B:
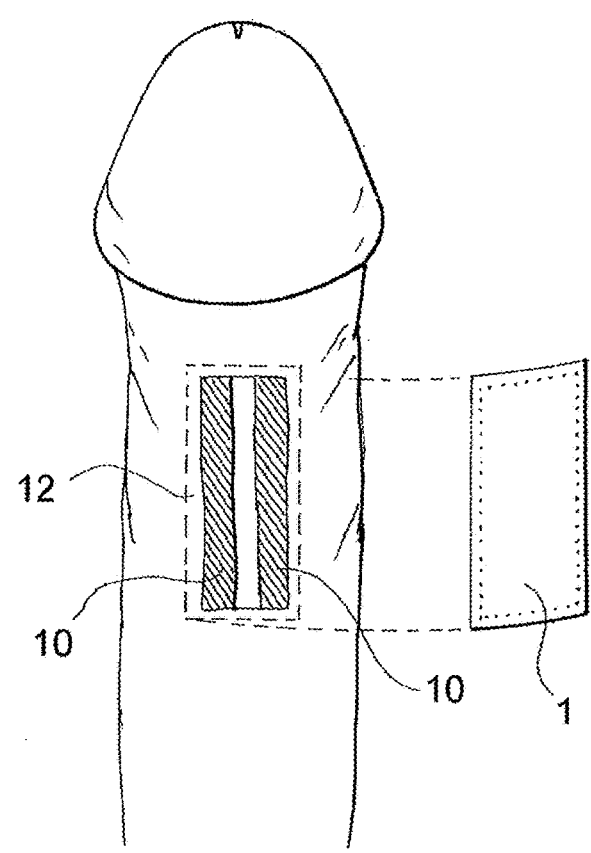

The graft 1 in accordance with the invention is intended to be placed over the corpora cavernosa 10 (FIGS. 2a-2c, 3) after having removed the IPP plaque 11 (FIG. 3) and be sutured in proximity of the tunica albuginea 12, after having performed an incision of the dermis 15 (FIG. 3) and of Buck's fascia 14 (FIG. 3) according to known surgery techniques.

Said graft (1) can be sutured to the incision by means of suture thread with diameter of 3/0 or 4/0, in resorbable material. The thread for suturing this graft is preferably of the same material used for making the fabric of the graft.

The main advantage of a graft in PGA is its resorbability during the regeneration of the removed area and therefore it is not necessary to remove said graft as instead takes place for the graft in silicone covered in turhostratic carbon. Moreover it does not lead to risks of infection and the quality of the reepithelialization is high.

Moreover this graft in PGA does not have any risk of adherence of the fibrotic capsule to the graft in that it is completely resorbable in a period of 1-2 months for the PGA on the basis of the metabolism.

Additionally the PGA has the advantage of resorbing, leaving room for a new elastic autologous tissue like the original one.

It is to be noted that the present graft 1 is implanted in the patient without having been previously coated with a deposition of cells, without any surface treatment in order to encourage the engraftment of the growing tissues since it has proved to be suitable, after the insertion inside the patient, for making grow thereon only autologous cells generated by the process of tissue reconstruction of the corpora cavernosa and/or of the tunica albuginea of the patient which takes place only after the insertion of the graft as is.

This is found to be an advantage compared to synthetic grafts which however use bioabsorbable three-dimensional matrices of high porosity for the same application, said matrices acting as substrate in order to be covered by cells grown in vitro of the organ to be repaired in order to obtain a piece of biological tissue which will then be implanted in place of the portion of diseased tissue. This procedure, while allowing excellent results to be obtained in terms of compatibility and mechanical performances, is very complicated, with long performance times, and costly.

Numerous detailed modifications and changes, within the reach of a person skilled in the art, may be made to the present embodiments of the invention, in any case coming within the scope of the invention disclosed by the appended claims.

The invention claimed is:

1. Bioabsorbable graft (1) for use in permanent implant after excision of a IPP (induratio penis plastica) plaque due to Peyronie's disease, consisting of a fabric (2) having a low porosity equal to or lower than 50%, said fabric deriving from a yarn of fibres made of a resorbable polymer of PGA (polyglycolide), having a thickness lower than 600 microns, said graft (1) having a planar flat form, the graft being a loom woven fabric made without reinforcements and/or support structure, said graft (1) in woven fabric is inherently capable without further modification of being impermeable to arteria blood and of being implanted without any deposition of tissue cells on its surface.

2. Graft (1) according to claim 1 wherein said woven fabric (2) in PGA is formed with a multifilament or with a monofilament yarn having a basis weight lower than 120 deniers.

3. Graft (1) according to claim 2 wherein a monofilament of PGA is used, and the fabric (2) has a basis weight lower than 240 deniers and the monofilament of PGA has a denier count lower than 120 deniers.

4. Graft (1) according to claim 2 wherein a multifilament yarn in PGA is used, and it is a multifilament yarn of 75 deniers/30 filaments.

5. Graft (1) according to claim 2, having a rectangular or square form in plan view.

6. Graft (1) according to claim 1 wherein a monofilament of PGA is used, and the fabric (2) has a basis weight lower than 240 deniers and the monofilament of PGA has a denier count lower than 120 deniers.

7. Graft (1) according to claim 6 wherein a multifilament yarn in PGA is used, and it is a multifilament yarn of 75 deniers/30 filaments.

8. Graft (1) according to claim 6, having a rectangular or square form in plan view.

9. Graft (1) according to claim 1 wherein a multifilament yarn in PGA is used, and it is a multifilament yarn of 75 deniers/30 filaments.

10. Graft (1) according to claim 9, having a rectangular or square form in plan view.

11. Graft (1) according to claim 1, having a rectangular or square form in plan view.

12. The graft of claim 11, wherein the graft is in a rectangular form having dimensions of 5 cm×10 cm.

13. Graft (1) according to claim 1 wherein said woven fabric (2) comprises a plain weave.

14. Graft (1) according to claim 1 wherein said woven fabric (2) has a warp density—ends per cm or EPC—which is comprised between 50-100 ends/cm, and a weft density—counts per cm or CPC—which is comprised within a range of 30-70 counts/cm.

15. Graft (1) according to claim 1 wherein the porosity of said woven fabric (2) is within the range from 5% to 50%.

* * * * *